US012605331B2

(12) United States Patent
Cho

(10) Patent No.: US 12,605,331 B2
(45) Date of Patent: Apr. 21, 2026

(54) COMPOSITION COMPRISING IRIS-DERIVED EXOSOME AS ACTIVE INGREDIENT

(71) Applicant: ExoCoBio Inc., Cheongju-si (KR)

(72) Inventor: Byong Seung Cho, Anyang-si (KR)

(73) Assignee: ExoCoBio Inc., Cheongju-si (KR)

( * ) Notice: Subject to any disclaimer, the term of this patent is extended or adjusted under 35 U.S.C. 154(b) by 263 days.

(21) Appl. No.: 18/397,644

(22) Filed: Dec. 27, 2023

(65) Prior Publication Data

US 2024/0180816 A1 Jun. 6, 2024

Related U.S. Application Data

(63) Continuation of application No. PCT/KR2022/011554, filed on Aug. 4, 2022.

(30) Foreign Application Priority Data

Aug. 18, 2021 (KR) ........................ 10-2021-0108603

(51) Int. Cl.

| | |
|---|---|
| *A61K 8/9794* | (2017.01) |
| *A61K 8/02* | (2006.01) |
| *A61K 8/14* | (2006.01) |
| *A61K 36/88* | (2006.01) |
| *A61P 29/00* | (2006.01) |
| *A61Q 19/02* | (2006.01) |
| *A61Q 19/08* | (2006.01) |

(52) U.S. Cl.
CPC .......... *A61K 8/9794* (2017.08); *A61K 8/0212* (2013.01); *A61K 8/14* (2013.01); *A61K 36/88* (2013.01); *A61P 29/00* (2018.01); *A61Q 19/02* (2013.01); *A61Q 19/08* (2013.01); *A61K 2800/56* (2013.01); *A61K 2800/884* (2013.01)

(58) Field of Classification Search
None
See application file for complete search history.

(56) References Cited

U.S. PATENT DOCUMENTS

| | | | |
|---|---|---|---|
| 5,795,574 A | 8/1998 | Breton et al. | |
| 6,224,850 B1 | 5/2001 | Breton et al. | |
| 6,419,962 B1 | 7/2002 | Yokoyama et al. | |
| 6,471,997 B1 * | 10/2002 | Breton ..................... | A61K 8/27 |
| | | | 424/773 |
| 2017/0209365 A1 | 7/2017 | Cho et al. | |
| 2018/0271773 A1 * | 9/2018 | Lee ......................... | A61P 17/00 |
| 2019/0247287 A1 * | 8/2019 | Pinsky .................. | A61K 47/42 |
| 2021/0121393 A1 | 4/2021 | Yi et al. | |

FOREIGN PATENT DOCUMENTS

| | | | | |
|---|---|---|---|---|
| EP | 0815838 | A2 | 1/1998 | |
| EP | 4378449 | A1 | 6/2024 | |
| JP | 09-030954 | A | 2/1997 | |
| JP | 9-124499 | A | 5/1997 | |
| KR | 10-1998-0079285 | A | 11/1998 | |
| KR | 10-2007-0002133 | A | 1/2007 | |
| KR | 10-2007-0115507 | A | 12/2007 | |
| KR | 10-2016-0086253 | A | 7/2016 | |
| KR | 10-2058444 | B1 | 12/2019 | |
| KR | 10-2257524 | B1 | 5/2021 | |
| KR | 10-2348510 | B1 | 1/2022 | |
| WO | WO-2014102483 | A2 * | 7/2014 | ............. A61Q 19/00 |

OTHER PUBLICATIONS

English Translation of WO2014/102483 (Jul. 3, 2014).*
International Search Report for PCT/KR2022/011554 dated Nov. 11, 2022 [PCT/ISA/210].

* cited by examiner

*Primary Examiner* — Bong-Sook Baek
(74) *Attorney, Agent, or Firm* — Sughrue Mion, PLLC

(57) ABSTRACT

A composition containing *iris*-derived exosomes as an active ingredient is provided for skin elasticity improvement, skin wrinkle reduction, skin regeneration, skin tone improvement, skin brightness improvement, skin whitening, anti-inflammation, wound healing and/or wound healing acceleration.

17 Claims, 8 Drawing Sheets
(3 of 8 Drawing Sheet(s) Filed in Color)

Collagen assay

*;p<0.05
;p<0.05

Anti-Inflammation

COMPOSITION COMPRISING IRIS-DERIVED EXOSOME AS ACTIVE INGREDIENT

CROSS REFERENCE

This application is a Bypass Continuation of International Application No. PCT/KR2022/011554 filed Aug. 4, 2022, claiming priority based on Korean Patent Application No. 10-2021-0108603 filed Aug. 18, 2021, the entire contents of which are incorporated herein by reference.

TECHNICAL FIELD

The present invention relates to a novel composition comprising exosomes derived from *iris* as an active ingredient, and more specifically, to a composition for skin elasticity improvement, skin wrinkle reduction, skin regeneration, skin tone improvement, skin brightness improvement, skin whitening, anti-inflammation, wound healing and/or wound healing acceleration comprising exosomes derived from *iris* as an active ingredient.

Moreover, the present invention relates to a cosmetic composition for skin elasticity improvement, skin wrinkle reduction, skin regeneration, skin tone improvement, or skin brightness improvement and/or skin whitening comprising said composition, and to a pharmaceutical composition for anti-inflammation, wound healing and/or wound healing acceleration comprising said composition.

BACKGROUND ART

It is known that skin aging leads to a decrease in skin elasticity and an increase in skin wrinkles and that the decrease in skin elasticity and the formation of skin wrinkles occur due to decreased synthesis of collagen and stimulated expression of the collagenase matrix metalloproteinase (MMP).

In addition, it is known that in skin cells, COX-2, an enzyme that produces inflammatory cytokines increases due to aging progression or ultraviolet (UV) rays, resulting in increased synthesis of prostaglandin E2 and increased production of inflammation inducers. Due to inflammatory reactions, the biosynthesis of MMP increases, causing collagen degradation and resulting in the decrease in skin elasticity and the formation of skin wrinkles. In particular, when sunlight and ultraviolet rays are irradiated directly onto skin, a lot of free radicals are generated, and these free radicals could damage the antioxidant defense system of skin, thus increasing wrinkles, making skin loose and accelerating skin aging. Substances known to be effective in reducing skin wrinkles include adenosine and retinoic acid. However, adenosine has little efficacy in clinical practice, and retinoic acid cannot be used for pregnant women and has side effects such as erythema.

Human skin color is determined by the concentration and distribution of melanin in the skin. Melanin is synthesized through a non-enzymatic oxidation reaction after conversion from tyrosine to DOPA and dopaquinone by tyrosinase. When melanin is excessively produced, pigmentation occurs, and then melasma, spots and freckles appear on face, neck, arms and the like, which are not good for appearance. Although skin whitening agents are being developed to improve melasma, freckles and dark skin tone, it is difficult to develop skin whitening agents that have an excellent whitening effect and have no side effect. For example, a skin whitening agent that selectively attacks melanocytes that produce melanin has an excellent whitening effect, but has a side effect of skin toxicity.

Inflammation is a defense response of the body against physical or chemical injury, infection with bacteria, fungi or viruses, or pathological conditions caused by various allergens and the like. Inflammatory response appears as part of innate immune response. Various substances and physiological and chemical phenomena are involved in inflammatory response, and recent studies have shown that various inflammatory cytokines play an important role in inflammatory response. Major cytokines involved in inflammatory response include IL-1β, TNF-α, IL-6, IL-8, IL-12, IFN-β, and the like. The increased expression and secretion of these cytokines and the activation thereof are associated with a series of complex physiological responses, including secretion of inflammatory mediators, immune cell infiltration, cell migration, and tissue destruction, as well as symptoms such as erythema, edema, fever and pain.

In general, inflammatory response does not become a significant problem and the affected area returns to its normal state, if the infectious agent is removed from the body and the damaged tissue is regenerated. However, if the infectious agent is not removed from the body or the inflammatory response is excessive or persistent due to internal substances of the body, acute or chronic inflammatory disease occurs. Non-steroidal anti-inflammatory drugs, steroidal anti-inflammatory drugs, antagonists of neuropeptides, COX inhibitors, anti-histamines, and immunosuppressive drugs such as cyclosporine A are used for alleviation or treatment of inflammatory response or inflammatory diseases caused thereby, but have problems that they cause adverse effects such as skin atrophy, vasodilation, depigmentation, hypersensitivity reactions, tolerance, neutropenia and the like. In addition, there is a limit that the aforesaid drugs merely help to control symptoms related to inflammation to a certain level rather than the underlying treatment therefor.

Recently, there have been reports that cell secretomes contain various bioactive molecules that regulate cellular behaviors. In particular, cell secretomes contain 'exosome' that has intercellular signaling functions, and thus studies on the components and functions thereof have been actively conducted.

Cells shed various membraneous vesicles to their extracellular environment, and these released vesicles are usually called extracellular vesicles (EVs). The EV is also called cell membrane-derived vesicle, ectosome, shedding vesicle, microparticle, exosome, etc., and is also used discriminately from exosome in some cases.

Exosome is a vesicle of tens to hundreds of nanometers in size, which comprises a phospholipid bilayer membrane having the same structure as that of the cell membrane. This exosome contains proteins, nucleic acids (mRNA, miRNA, etc.) and the like which are called exosome cargo. It is known that exosome cargo includes a wide range of signaling factors, and these signaling factors are specific for cell types and regulated differently depending on secretory cells' environment. It is known that exosome is an intercellular signaling mediator secreted by cells, and various cellular signals transmitted through it regulate cellular behaviors, including the activation, growth, migration, differentiation, dedifferentiation, apoptosis, and necrosis of target cells. Exosome contains specific genetic materials and bioactive factors depending on the nature and state of cells from which the exosome was derived. Exosome derived from proliferating stem cells regulates cell behaviors such as cell migration, proliferation and differentiation, and recapitulates the characteristics of stem cells involved in tissue regeneration (Nature Review Immunology 2002 (2) 569-579).

That is, exosomes called "avatars" of cells contain bioactive factors such as growth factors, similar to cells, and serve as carriers that transmit bioactive factors between cells, that is, serve to mediate cell-to-cell communication. Exosomes are known to be released not only from animal cells such as stem cells, immune cells, fibroblasts and cancer cells, but also from cells of various organisms such as plants, bacteria, fungi, and algae. For example, exosomes may be isolated from culture media of plant cells or plant stem cells, as well as culture media of cancer cells, immune cells, mesenchymal stem cells, and the like.

However, studies on the isolation, purification, and characterization of exosomes derived from plant cells or plant stem cells remain insufficient, and most of these studies are merely used for marketing purposes where extracellular vesicles mixed in the filtrate of plant juice are simply called exosomes. Therefore, more detailed characterization and functional studies of exosomes derived from plant cells are required.

*Iris* (*Iris* sp.) is a perennial herbaceous plant belonging to the family Iridaceae, in the order Liliales and the class Monocotyledoneae. *Iris* is distributed in various regions depending on the species thereof. For example, *Iris nertsch-inskia* is distributed in Korea, Japan, northeastern China, and eastern Siberia, and is native to dry areas at the feet of mountains. Among *iris* extracts, isoflavone-based substances have been reported to exhibit anticancer or anti-inflammatory effects, but the components and mechanisms of action of *iris* extracts have not been clearly identified. Therefore, accurate component analysis of *iris* and scientific investigation of pharmacological mechanism of action thereof are necessary. Current technology remains at the level of using extracts, obtained by hot water extraction or solvent extraction of *iris* flowers, leaves, stems, roots and the like, as cosmetic ingredients. However, solvent extracts have the problem of being toxic to the human body due to residual extraction solvents.

Recently, research has been conducted on cosmetic materials using callus, called plant stem cells. In this regard, a technology of using culture media of callus obtained by culturing the callus induced by wounding *iris* flowers, leaves or the like has been introduced, but this technology is also merely at a level where culture media of callus themselves or extracts obtained by drying the callus and then subjecting the dried callus to hot-water extraction or solvent extraction are used as cosmetic ingredients. Further, culture media of callus contain growth regulators or a callus-inducing substance, and thus are hardly regarded as natural cosmetic ingredients, and the growth regulators contained in the culture media may cause side effects such as skin troubles.

The present inventor has found that exosomes derived from *iris* are effective in skin elasticity improvement, skin wrinkle reduction, skin regeneration, skin tone improvement, skin brightness improvement, skin whitening, anti-inflammation, wound healing and/or wound healing acceleration, and has developed a cosmetic composition for skin elasticity improvement, skin wrinkle reduction, skin regeneration, skin tone improvement, skin brightness improvement and/or skin whitening and a pharmaceutical composition for anti-inflammation, wound healing and/or wound healing acceleration, containing exosomes derived from *iris* as an active ingredient.

Meanwhile, it is to be understood that the matters described as the background art are intended merely to aid in the understanding of the background of the present invention and are not admitted as prior art against the present invention.

SUMMARY OF INVENTION

An object of the present invention is to provide a composition for skin elasticity improvement, skin wrinkle reduction, skin regeneration, skin tone improvement, skin brightness improvement, skin whitening, anti-inflammation, wound healing and/or wound healing acceleration, containing exosomes derived from *iris* as an active ingredient.

Another object of the present invention is to provide a cosmetic composition for skin elasticity improvement, skin wrinkle reduction, skin regeneration, skin tone improvement, skin brightness improvement and/or skin whitening comprising said composition, and a pharmaceutical composition for anti-inflammation, wound healing and/or wound healing acceleration comprising said composition.

However, the objects of the present invention as described above are illustrative and the scope of the present invention is not limited thereby. In addition, other objects and advantages of the present invention will be more apparent from the following description, the appended claims and the accompanying drawings.

BRIEF DESCRIPTION OF DRAWINGS

The patent or application file contains at least one drawing executed in color. Copies of this patent or patent application publication with color drawing(s) will be provided by the Office upon request and payment of the necessary fee.

DETAILED DESCRIPTION OF INVENTION

Figure 1:
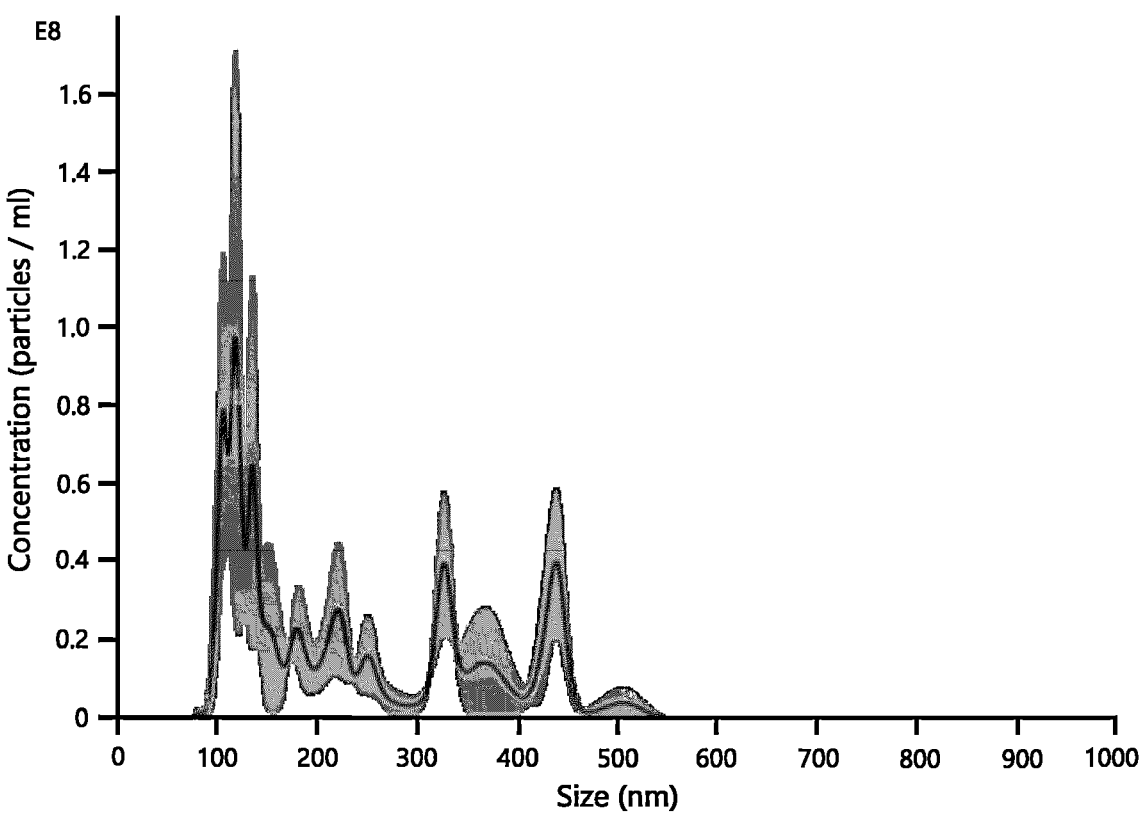
FIG. 1 is a graph showing the particle size distribution and particle number obtained by performing nanoparticle tracking analysis (NTA) of the exosomes derived from *iris* of the present invention.

The present invention provides a composition for skin elasticity improvement, skin wrinkle reduction, skin regeneration, skin tone improvement, skin brightness improvement, skin whitening, anti-inflammation, wound healing and/or wound healing acceleration, containing exosomes derived from *iris* as an active ingredient.

As used herein, the term "*iris*" refers to a plant belonging to *Iris* sp. For example, *Iris* sp. plant may be *Iris ensata, Iris pallida, Iris versicolor, Iris florentina, Iris nertschinskia, Iris pseudacorus, Iris setosa, Iris lactea, Iris germanica*, or *Iris odaesanensis*.

As used herein, the term "topical administration" for example means to apply or spread a composition that is suitable for topical application, onto the surface of skin including the scalp, not limited thereto. Thus, the "topical administration" includes administering a composition to the skin and/or scalp by topical routes such as injection, microneeding, spread, spray, transdermal delivery using a patch or a sheet, iontophoresis, and the like.

As used herein, the term "exosomes" refers to nano-sized vesicles secreted or released from plant cells into extracellular spaces and having a membrane structure, and is also referred to as exosome-like vesicles or exosome-like particles.

As used herein, the term "skin elasticity" refers to a feature in which skin deformed by an external force easily returns to its original shape when the external force is removed. The term "skin wrinkles" refers to fine lines caused by skin aging. Skin wrinkles may be caused by genetic factors, reduction in collagen and elastin present in the skin dermis, external environmental factors, or the like. Accordingly, the term "skin wrinkle reduction or improvement" as used herein refers to suppressing or inhibiting the formation of wrinkles on the skin, or reducing already formed wrinkles.

Meanwhile, the term "skin tone", as used herein, refers to the darkness or lightness of skin color. As used herein, the term "skin whitening" includes increasing the brightness of the skin whose brightness has decreased due to an excess of pigments such as melanin, or maintaining the brightness of the skin at a certain level.

As used herein, the term "anti-inflammation" means prevention, suppression, alleviation, amelioration or treatment of inflammation. As an example, not limiting the present invention, examples of inflammatory diseases include dermatitis, atopic dermatitis, eczema, inflammation caused by bacterial, viral or fungal infections, burns, inflammation caused by burns, wounds, inflammation caused by wounds, and the like.

As used herein, the term "wound" means a condition in which a part or all of the body is injured, and is intended to encompass pathological conditions in which a tissue constituting an inside or an external surface of the body, for example, skin, muscle, nerve tissue, bone, soft tissue, internal organ, or blood vessel tissue, is damaged or destroyed. As an example, not limiting the present invention, examples of the wound include abrasion, laceration, stab wound, incised wound, avulsion, bedsore, tissue destruction caused by irradiation, penetrated wound, gunshot wound, burn, frostbite, surgical wound, sutures after plastic surgery, wound caused by chemical substance and so on, and may include any damage to any part of an individual.

As used herein, the term "iontophoresis" refers to a method of flowing a microcurrent through a skin to which an active ingredient has been applied, generating a potential difference thereby and changing the electrical environment of the skin, and thus allowing an ionized active ingredient to penetrate the skin by electrical repulsion. Examples of iontophoresis that is used in one embodiment of the present invention include: a method of introducing a microcurrent into a skin by allowing the microcurrent to flow from an external power source into an electrode patch on the skin, the microcurrent being generated by the external power source; a method of introducing a microcurrent into a skin, the microcurrent being generated by a battery provided in an electrode patch on the skin; and a method of introducing a microcurrent into a skin through a patch on the skin provided with a reverse electrodialysis device, the microcurrent being generated by the concentration difference between high concentration electrolyte solution and low concentration electrolyte solution in the reverse electrodialysis device. However, the present invention is not limited thereto, and various types of iontophoresis may, of course, be used.

As used herein, the term "exosomes derived from *iris*" is meant to include all exosomes isolated from, for example, a culture medium of *iris* plant cells, a culture medium of *iris* callus, a culture medium of *iris* plant stem cells, *iris* juice, or a biological solution of *iris* equivalent thereto, or derived (e.g., secreted or released) from plant cells or plant stem cells of *iris*.

In the composition according to one embodiment of the present invention, the exosomes derived from *iris* may be obtained by isolation and purification from a culture medium of *iris* root-derived callus.

The composition containing exosomes derived from *iris* as an active ingredient according to one embodiment of the present invention may exhibit at least one effect of skin elasticity improvement, skin wrinkle reduction, skin regeneration, skin tone improvement, skin brightness improvement, skin whitening, anti-inflammation, wound healing and/or wound healing acceleration.

The composition containing exosomes derived from *iris* as an active ingredient according to the present invention may be a cosmetic composition or a pharmaceutical composition.

The present invention provides a cosmetic composition for skin elasticity improvement, skin wrinkle reduction, skin regeneration, skin tone improvement, skin brightness improvement and/or skin whitening, containing exosomes derived from *iris* as an active ingredient. For example, the cosmetic composition may be a shampoo, a soap, a rinse, a surfactant-containing cleanser, a cream, a lotion, an ointment, a tonic, a treatment, a conditioner, a suspension, an emulsion, a paste, a gel, an oil, a wax, a spray, an aerosol, a mist, or a powder, and is preferably a lotion or a cream.

The present invention also provides a pharmaceutical composition for anti-inflammation, wound healing and/or wound healing acceleration, containing exosomes derived from *iris* as an active ingredient.

As an example not limiting the present invention, the pharmaceutical composition according to one embodiment of the present invention may be administered or treated by injection, microneedling, iontophoresis, application, or a combination thereof. For example, the pharmaceutical composition may be an injectable formulation, an infusion formulation, a spray formulation, a liquid formulation, or a patch formulation.

In one embodiment of the present invention, when the composition is used as a pharmaceutical composition, it may include pharmaceutically acceptable carriers, excipients or diluents. The carriers, excipients and dilutes include, but are not limited to, lactose, dextrose, trehalose, sucrose, sorbitol, mannitol, xylitol, erythritol, maltitol, starch, acacia gum, alginate, gelatin, calcium phosphate, calcium carbonate, calcium silicate, cellulose, methyl cellulose, microcrystalline cellulose, polyvinyl pyrrolidone, water, methyl hydroxybenzoate, propyl hydroxybenzoate, talc, magnesium stearate, and mineral oil. In addition, the effective amount of the pharmaceutical composition according to one embodiment of the present invention means the amount required for administration in order to achieve the effects of anti-inflammation, wound healing and/or wound healing acceleration.

The content of the pharmaceutical composition according to one embodiment in a formulation may be suitably selected depending on the kind, amount, form and the like of additional components as described above. For example, the pharmaceutical composition of the present invention may be contained in an amount of about 0.1 to 99 wt %, preferably about 10 to 90 wt %, based on the total weight of an injectable formulation. Furthermore, the suitable dose of the pharmaceutical composition according to one embodiment of the present invention may be adjusted depending on the severity of disease, the type of formulation, formulating method, patient's age, sex, body weight, health condition, diet, excretion rate, the period of administration, and the regime of administration. For example, when the pharmaceutical composition according to one embodiment of the present invention is administered to an adult, it may be administered once to several times at a dose of 0.001 mg/kg to 100 mg/kg per day.

Meanwhile, when the composition according to one embodiment of the present invention is prepared as a cosmetic composition, it may suitably contain components which are generally used in cosmetic products, for example, moisturizers, antioxidants, oily components, UV absorbers, emulsifiers, surfactants, thickeners, alcohols, powder components, colorants, aqueous components, water, and various skin nutrients, etc., as needed, within the range that does not impair the effect of the present invention.

Furthermore, the cosmetic composition according to one embodiment of the present invention may include, in addition to the exosomes derived from *iris*, an agent for improving skin condition, an antioxidant, an anti-aging agent, a whitening agent and/or a moisturizer, which have been used in the prior art, within the range that does not impair the effects (e.g., skin elasticity improvement, skin wrinkle reduction, skin regeneration, skin tone improvement, skin brightness improvement, skin whitening, skin beauty, etc.).

The cosmetic composition according to one embodiment of the present invention may be used in various forms, for example, a patch, a mask pack, a mask sheet, a cream, a tonic, an ointment, a suspension, an emulsion, a paste, a lotion, a gel, an oil, a pack, a spray, an aerosol, a mist, a foundation, a powder, and an oilpaper.

The cosmetic composition according to one embodiment of the present invention may be used for the purpose of skin elasticity improvement, skin wrinkle reduction, skin regeneration, skin tone improvement, skin brightness improvement and/or skin whitening, and may be prepared as any formulation which is generally prepared in the art. For example, it may be formulated as a patch, a mask pack, a mask sheet, a skin softener, a nutrition, an astringent lotion, a nourishing cream, a massage cream, an eye cream, a cleansing cream, an essence, an eye essence, a cleansing lotion, a cleansing foam, a cleansing water, a sunscreen, a lipstick, a soap, a shampoo, a surfactant-containing cleanser, a bath preparation, a body lotion, a body cream, a body oil, a body essence, a body cleanser, a hairdye, a hair tonic, etc., without being limited thereto.

The cosmetic composition according to one embodiment of the present invention may contain components which are commonly used in cosmetic products. For example, the cosmetic composition may contain conventional adjuvants and carriers, such as antioxidants, stabilizers, solubilizers, vitamins, pigments, and fragrances. In addition, other components in each formulation for the cosmetic composition may be suitably selected without difficulty by those skilled in the art depending on the type or intended use of the cosmetic composition.

Another embodiment of the present invention provides a cosmetic method for regulating mammalian skin conditions, except for treatment purposes, using the cosmetic composition. In the cosmetic method of the present invention, the expression "regulating skin conditions" means improving skin conditions and/or prophylactically regulating skin conditions, and the expression "improving skin conditions" means a visually and/or tactilely perceivable positive change in the appearance and feeling of skin tissue. For example, the expression "improving skin conditions" may include skin elasticity improvement, skin wrinkle reduction, skin regeneration, skin tone improvement, skin brightness improvement, and/or skin whitening.

The cosmetic method according to one embodiment of the present invention includes: (a) applying the cosmetic composition directly to a mammalian skin; or (b) contacting or attaching a patch, a mask pack or a mask sheet, which has the cosmetic composition applied thereto or soaked therein, to the mammalian skin; or sequentially performing (a) and (b). In step (a), the cosmetic composition may be a lotion or a cream.

Alternatively, the cosmetic method according to one embodiment of the present invention may further comprise (c) removing the patch, the mask pack or the mask sheet from the mammalian skin after step (b), and applying the cosmetic composition to the mammalian skin. In step (c), the cosmetic composition may be a lotion or a cream.

In the cosmetic method according to one embodiment of the present invention, the mammal may be a human, a dog, a cat, a rodent, a horse, a cattle, a monkey, or a pig.

In addition, the present invention provides a method for treating inflammation, healing wound or accelerating wound healing, the method comprising administering a therapeutically effective amount of the pharmaceutical composition to a mammal, or applying the pharmaceutical composition to a skin, an inflammatory area, or a wounded area. The mammal may be a human, a dog, a cat, a rodent, a horse, a cattle, a monkey, or a pig.

Advantageous Effects

The composition according to the present invention is less likely to contain impurities such as residual solvents or growth regulators compared to conventional hot-water extracts or solvent extracts of *iris*, filtrates of such extracts, and culture media of *iris* callus, and has excellent effects on skin elasticity improvement, skin wrinkle reduction, skin regeneration, skin tone improvement, skin brightness improvement, skin whitening, anti-inflammation, wound healing, or wound healing acceleration.

It should be understood that the scope of the present invention is not limited to the aforementioned effects.

EXAMPLES

Hereinafter, the present invention will be described in more detail with reference to the following examples. However, the following examples are only to illustrate the present invention and are not intended to limit or restrict the scope of the present invention. Those that can be easily inferred by those skilled in the art from the detailed description and examples of the present invention are interpreted as falling within the scope of the present invention. References referred to in the present invention are incorporated herein by reference.

Throughout the present specification, it is to be understood that, when any part is referred to as "comprising" any component, it does not exclude other components, but may further include other components, unless otherwise specified.

Example 1: Preparation of Culture Media of *Iris* Callus

According to preparation and culture methods for plant stem cells known in the art, calluses were induced from *iris* roots, and cells of the induced *iris* callus were cultured. In addition, a callus having a good growth state was selected and cultured in large amounts, thereby preparing culture media (conditioned media) of *iris* callus.

Example 2: Preparation of *Iris*-Derived Exosomes

The culture media of *iris* callus (culture media of *Iris germanica* callus) prepared as described in Example 1 were purchased from Biospectrum Corporation (located in Gyeonggi-do, Korea and supplying culture media of *iris* callus). The culture media of *iris* callus were filtered through a 0.22 m filter to remove impurities such as cell debris, waste products and large particles. *Iris*-derived exosomes were isolated from the filtered culture media by tangential flow filtration (TFF) method.

The size and concentration of the isolated *iris*-derived exosomes were analyzed by nanoparticle tracking analysis (NTA) using NS300 (purchased from Malvern Panalytical) (FIG. 1).

Figure 2:
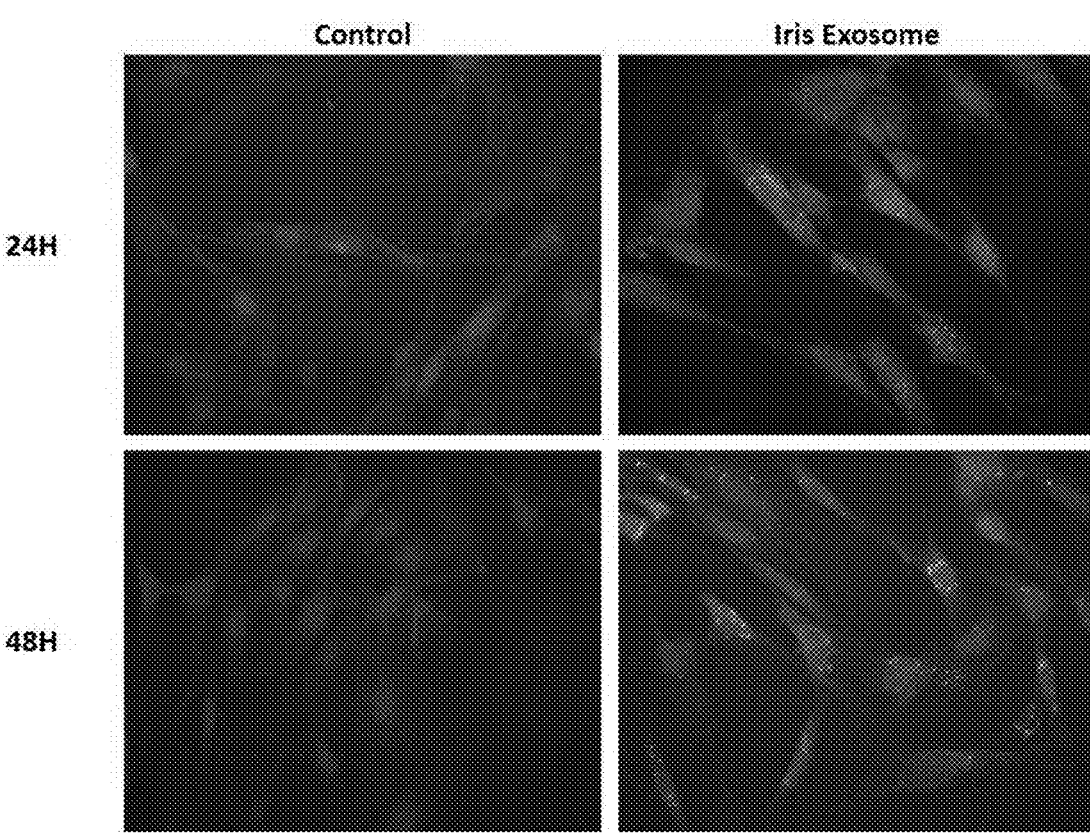
FIG. 2 depicts fluorescence microscopic images of cells showing that fluorescence-stained exosomes derived from *iris* were delivered into human dermal fibroblasts (green: exosomes delivered into cells; and blue: cell nucleus).

Example 3: Evaluation of Delivery Ability of *Iris*-Derived Exosomes into Dermal Fibroblasts In order to examine whether the *iris*-derived exosomes would be delivered into human dermal fibroblasts (purchased from ATCC), the following analysis was performed. To fluorescence-stain the membrane of the *iris*-derived exosomes prepared in Example 2, the exosomes were allowed to react with PKH67 fluorescence dye (purchased from Sigma-Aldrich). After the reaction, the reaction solution was fractionated with a MiniTrap-25 column (purchased from Cytiva) to remove free PHK67 that was not stained in the exosome membrane. A negative control was prepared by allowing PKH67 fluorescence dye to react with a buffered solution and fractionating the reaction product with a MiniTrap-25 column. The exosomes stained with PKH67 were incubated with pre-cultured human dermal fibroblasts, and then whether the exosomes would be delivered into the cells over time was observed using a fluorescence microscope. Hoechst fluorescence dye (purchased from Thermo Fisher) was used to stain the cell nucleus, and CellMask Orange fluorescence dye (purchased from Thermo Fisher) was used to stain the cytoplasm. As a result of examining whether the exosomes would be delivered into the cells, it was confirmed that the fluorescence-stained exosomes were delivered into the cells and green fluorescence accumulated in the cells over time (FIG. 2).

Example 4: Evaluation of Effect of Stimulating Collagen Production

Human dermal fibroblasts (purchased from ATCC) dispersed in DMEM medium containing fetal bovine serum were dispensed into a multiwell plate, and then cultured for 24 hours. Thereafter, the culture media of *iris* callus prepared in Example 1 or the *iris*-derived exosomes prepared in Example 2 were diluted in serum-free medium, and then the human dermal fibroblasts were treated with each of the dilutions and cultured for 24 hours. To evaluate the collagen production effect using human dermal fibroblasts, experimental groups were classified as follows:

(1) Negative control group (indicated as "N.C." in FIG. 3): an experimental group treated with a serum-free medium alone;

(2) Group treated with culture media of *iris* callus (indicated as "*Iris* Callus CM" in FIG. 3): an experiment group treated with the culture media of *iris* callus (prepared in Example 1) diluted in serum-free medium (treatment concentrations—low concentration: 60 μg/mL, and high concentration: 240 μg/mL); and (3) Group treated with *iris*-derived exosomes (indicated as "*Iris* Exosome" in FIG. 3): an experiment group treated with the *iris*-derived exosomes (prepared in Example 2) diluted in serum-free medium (treatment concentrations—low concentration: 60 μg/mL, and high concentration: 240 μg/mL).

According to each experimental group described above, the human dermal fibroblasts were treated and cultured for 24 hours. The culture media were collected and centrifuged, and then the centrifuged media were prepared. The amount of collagen, which was synthesized from the human dermal fibroblasts and accumulated in the culture media, was measured using an EIA kit (purchased from Takara) for procollagen type I C-peptide (PIP). The measured amount of collagen was normalized by dividing it by the total number of cells measured using an MTT assay kit (purchased from Sigma-Aldrich) to determine the relative amount of collagen.

Figure 3:
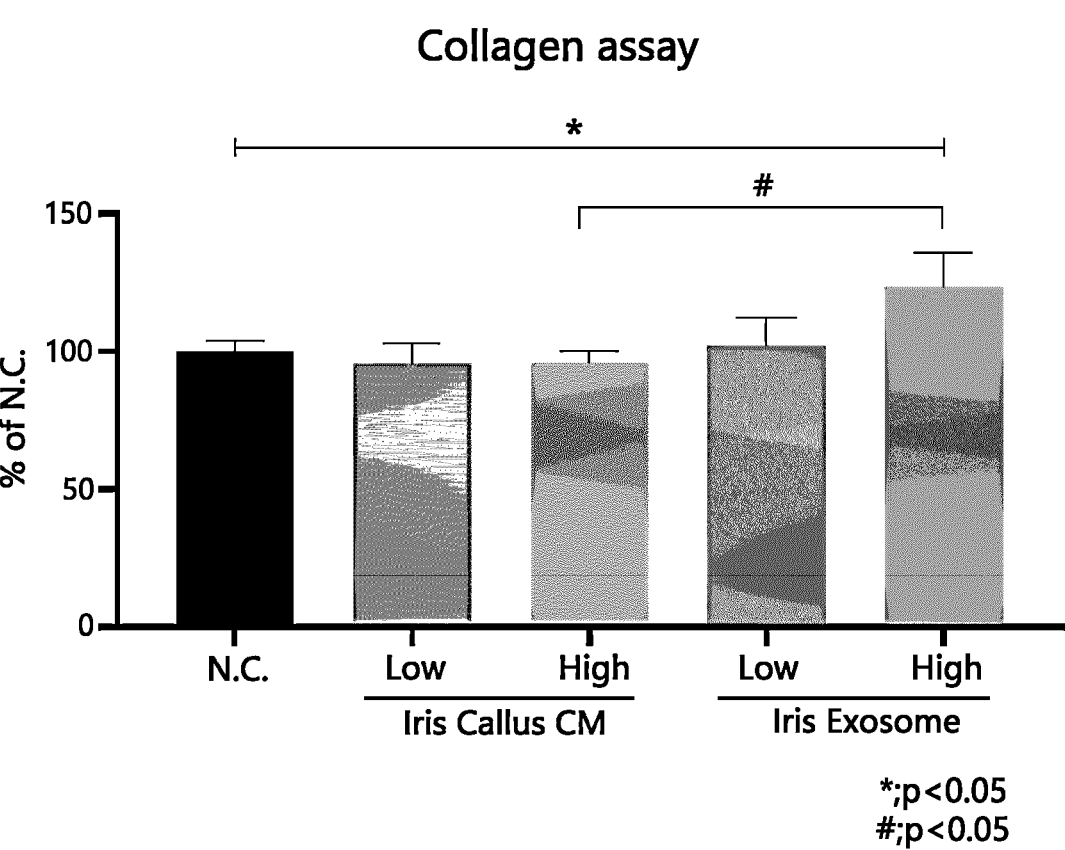
FIG. 3 is a graph showing that the relative amount of collagen increased after human dermal fibroblasts were treated with exosomes derived from *iris*.

As a result, it was confirmed that the group treated with the culture media of *iris* callus had no effect of increasing the collagen synthesis in the human dermal fibroblasts, compared to the negative control, whereas the *iris*-derived exosomes of the present invention increased the collagen synthesis in the human dermal fibroblasts. In particular, it was confirmed that the collagen synthesis in the human dermal fibroblasts remarkably increased when the cells were treated with a high concentration of the *iris*-derived exosomes (FIG. 3).

From the above experimental results, it can be seen that the *iris*-derived exosomes of the present invention have better effects on increasing the collagen synthesis, that is, skin elasticity improvement, wrinkle reduction and/or skin regeneration, than the culture media of *iris* callus.

As can be seen from the above results, the *iris*-derived exosomes of the present invention has a useful functional activity as a functional cosmetic for skin elasticity improvement, wrinkle reduction and/or skin regeneration, that is, an activity of increasing the collagen synthesis. Thus, the *iris*-derived exosomes of the present invention are useful as an active ingredient of a cosmetic composition for skin elasticity improvement, wrinkle reduction and/or skin regeneration.

Example 5: Evaluation of Skin Regeneration Effect Using Dermal Fibroblasts

To evaluate whether the exosomes prepared as described in Example 2 promotes wound healing in human dermal fibroblasts (purchased from ATCC), scratch-wound assay was performed. Human dermal fibroblasts dispersed in a DMEM containing fetal bovine serum were seeded into a culture plate for wound induction (ImageLock Plate; purchased from EssenBio) at a density of 5,000 cells/well and cultured for 24 hours at 37° C. under 5% $CO_2$. After the cells reached a confluency of 90% or more, scratches were made using a WoundMaker (purchased from EssenBio). To evaluate the skin regeneration effect using human dermal fibroblasts, experimental groups were classified as follows:

(1) Negative control group (indicated as "N.C." in FIG. 4): an experimental group treated with a serum-free medium alone;

(2) Positive control group (indicated as "P.C." in FIG. 4): an experimental group treated with a medium containing 10% fetal bovine serum;

(3) Group treated with culture media of iris callus (indicated as "Iris Callus CM" in FIG. 4): an experiment group treated with the culture media of iris callus (prepared in Example 1) diluted in serum-free medium (treatment concentrations—low concentration: 50 µg/mL, and high concentration: 200 µg/mL); and (4) Group treated with iris-derived exosomes (indicated as "Iris Exosome" in FIG. 4): an experiment group treated with the iris-derived exosomes (prepared in Example 2) diluted in serum-free medium (treatment concentrations—low concentration: 50 µg/mL, and high concentration: 200 µg/mL).

Thereafter, each of the experimental groups was subjected to Scratch-Wound, and the human dermal fibroblasts were cultured at 37° C. under 5% $CO_2$ for 24 hours. The wound healing efficacy in each experimental group was measured using Incucyte (purchased from Sartorius).

Figure 4:
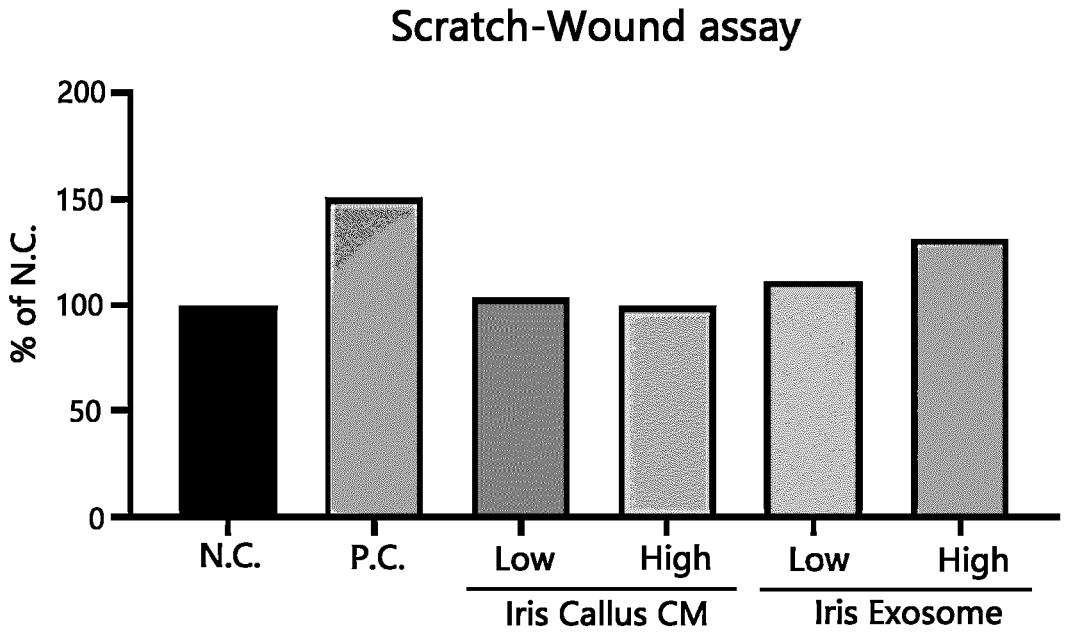
FIG. 4 is a graph showing that the migration of human dermal fibroblasts increased after scratch-wounds were treated with exosomes derived from *iris*.

As a result of measuring the wound healing efficacy, it was confirmed that the culture media of iris callus did not increase the migration of the human dermal fibroblasts, compared to the negative control, whereas the iris-derived exosomes of the present invention increased the migration of the human dermal fibroblasts, compared to the negative control (FIG. 4).

As can be seen from the above experimental results, the iris-derived exosomes of the present invention have an excellent effect of promoting the migration of human dermal fibroblasts, that is, an excellent wound healing effect or skin regeneration effect, as compared with the culture media of iris callus.

Therefore, the iris-derived exosomes of the present invention are useful as an active ingredient of a cosmetic composition for skin elasticity improvement, wrinkle reduction and/or skin regeneration, and as an active ingredient of a pharmaceutical composition for wound healing or wound healing acceleration.

Figure 5:
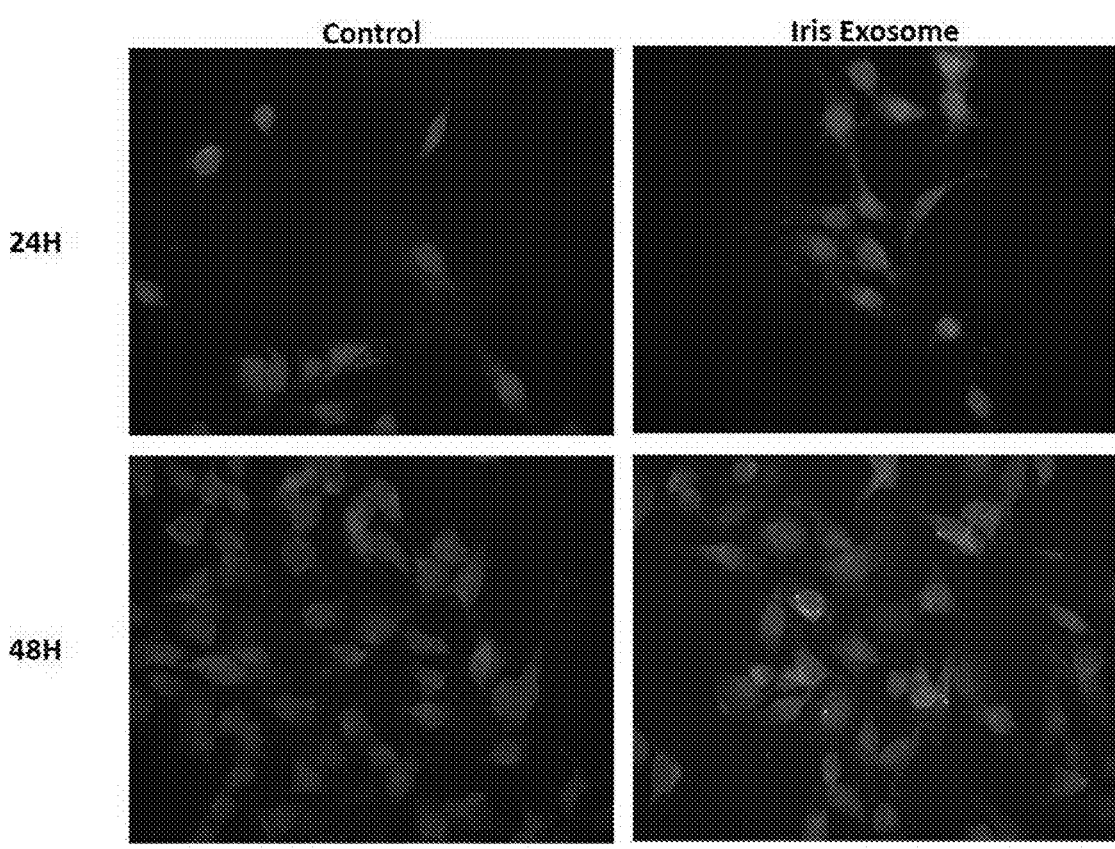
FIG. 5 depicts fluorescence microscopic images of cells showing that fluorescence-stained exosomes derived from *iris* were delivered into melanoma cells (green: exosomes delivered into cells; and blue: cell nucleus).

Example 6: Evaluation of Delivery Ability of Iris-Derived Exosomes into Melanoma Cells In order to examine whether the iris-derived exosomes would be delivered into mouse melanoma cells (B16F10; purchased from ATCC), the following analysis was performed. To fluorescence-stain the membrane of the iris-derived exosomes prepared in Example 2, the exosomes were allowed to react with PKH67 fluorescence dye (purchased from Sigma-Aldrich). After the reaction, the reaction solution was fractionated with a MiniTrap-25 column (purchased from Cytiva) to remove free PHK67 fluorescence dye that was not stained in the exosome membrane. A negative control was prepared by allowing PKH67 fluorescence dye to react with a buffered solution and fractionating the reaction product with a MiniTrap-25 column. The exosomes stained with PKH67 were incubated with pre-cultured mouse melanoma cells, and then whether the exosomes would be delivered into the cells over time was observed using a fluorescence microscope. Hoechst fluorescence dye (purchased from Thermo Fisher) was used to stain the cell nucleus, and CellMask Orange fluorescence dye (purchased from Thermo Fisher) was used to stain the cytoplasm. As a result of examining whether the exosomes would be delivered into the cells, it was confirmed that the fluorescence-stained exosomes were delivered into the cells and green fluorescence accumulated in the cells over time (FIG. 5).

Example 7: Melanogenesis Inhibitory Effect of Iris-Derived Exosomes

The whitening effect of the iris-derived exosomes was evaluated through the degree of inhibition of melanogenesis in melanoma cells. The melanoma cells are cells (B16F10; purchased from ATCC) derived from mouse melanoma and are cells that secrete a black pigment called melanin. Melanoma cells were seeded into a 48-well plate at 8,000 cells per unit area and cultured for 24 hours at 37° C. under 5% $CO_2$.

Thereafter, the culture media of iris callus prepared in Example 1 or the iris-derived exosomes prepared in Example 2 were diluted in a medium mixed with a-MSH, a melanin synthesis stimulant, and then melanoma cells were treated with the diluted culture media or exosomes and cultured for 48 hours. To evaluate the melanogenesis inhibitory efficacy using melanoma cells, the experimental groups were classified as follows:

(1) Negative control group (indicated as "N.C." in FIG. 6): an experimental group treated with a medium mixed with the melanin synthesis stimulant a-MSH;

(2) Positive control group (indicated as "P.C." in FIG. 6): an experimental group treated with a medium mixed with the melanin synthesis stimulant a-MSH and arbutin (final concentration 1 mM);

(3) Group treated with culture media of iris callus (indicated as "Iris Callus CM" in FIG. 6): an experimental group treated with a medium mixed with the culture media of iris callus (prepared in Example 1) and the melanin synthesis stimulant a-MSH (treatment concentrations of the culture media of iris callus—low concentration: 100 µg/mL, and high concentration: 200 µg/mL); and (4) Group treated with iris-derived exosomes (indicated as "Iris Exosome" in FIG. 6): an experimental group treated with a medium mixed with the iris-derived exosomes (prepared in Example 2) and the melanin synthesis stimulant a-MSH (treatment concentrations of the iris-derived exosomes—low concentration: 100 µg/mL, and high concentration: 200 µg/mL).

The melanoma culture medium according to each experimental group was recovered. The recovered melanoma culture medium was mixed with CCK-8 assay reagent (purchased from Dojindo) and the mixture was incubated for 2 hours at 37° C. under 5% $CO_2$. Then, the supernatant was transferred to a 96-well plate and the absorbance at 450 nm was measured to measure the total number of the cells. After washing the melanoma cells in the 48-well plate with a washing solution, the washed melanoma cells were treated with 1N NaOH (purchased from Merck-Millipore) mixed with 10% DMSO, and then the plate was sealed and heated for 20 minutes at 85° C. to extract melanin in the melanoma cells. The amount of extracted melanin was calculated by measuring the absorbance at 405 nm and normalized by the absorbance value measured through the CCK-8 assay.

Figure 6:
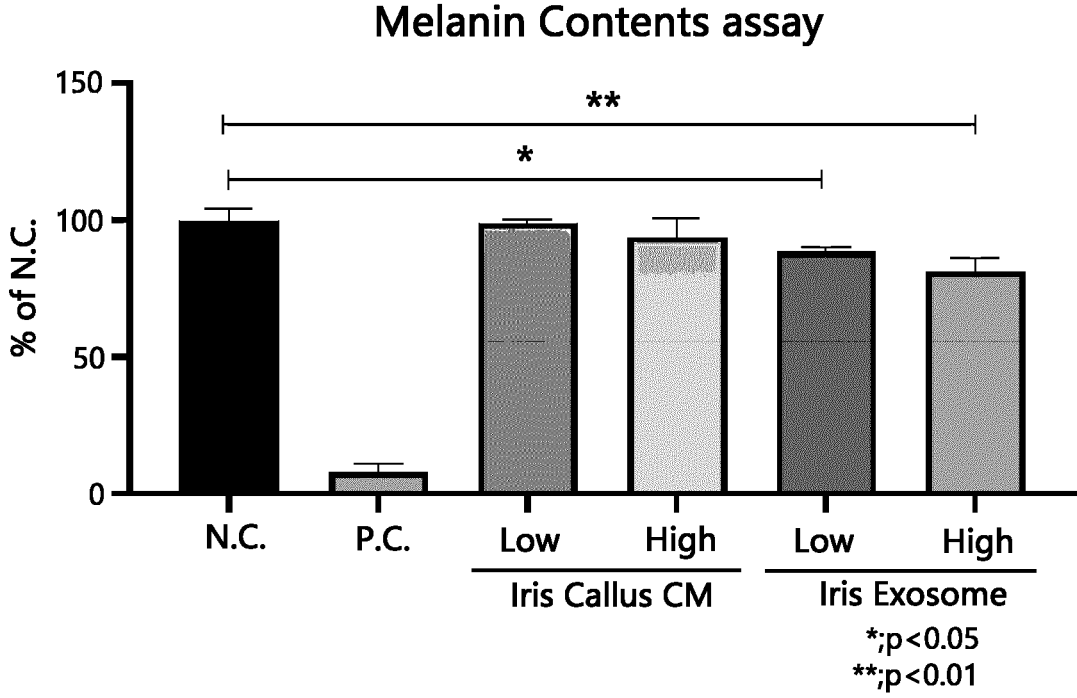
FIG. 6 is a graph showing that the amount of melanin production decreased in a concentration-dependent manner when melanoma cells were treated with exosomes derived from *iris*.

As a result, it was confirmed that the *iris*-derived exosomes of the present invention have the effect of inhibiting melanin synthesis in melanoma cells in a concentration-dependent manner, compared to the negative control, and have a better melanin synthesis inhibitory effect than the culture media of *iris* callus (FIG. 6).

Therefore, a cosmetic composition containing *iris*-derived exosomes as an active ingredient according to the present invention has a whitening effect, and the *iris*-derived exosomes of the present invention is useful as an active ingredient of a cosmetic composition for skin tone improvement, skin brightness improvement and/or skin whitening.

Figure 7:
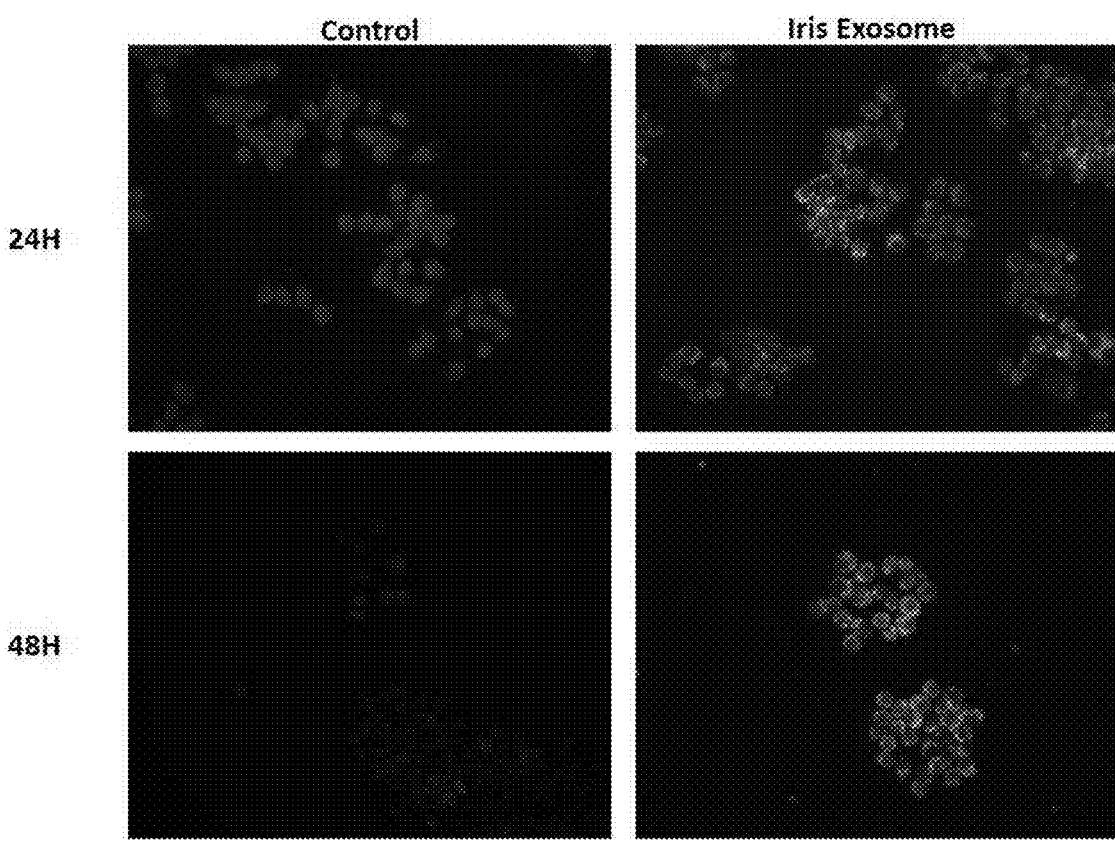
FIG. 7 depicts fluorescence microscopic images of cells showing that fluorescence-stained exosomes derived from *iris* were delivered into RAW 264.7 cells (green: exosomes delivered into cells; and blue: cell nucleus).

Example 8: Evaluation of Delivery Ability of *Iris*-Derived Exosomes into Macrophages In order to examine whether the *iris*-derived exosomes would be delivered into mouse macrophages (RAW 264.7; purchased from ATCC), the following analysis was performed. To fluorescence-stain the membrane of the *iris*-derived exosomes prepared in Example 2, the exosomes were allowed to react with PKH67 fluorescence dye (purchased from Sigma-Aldrich). After the reaction, the reaction solution was fractionated with a MiniTrap-25 column (purchased from Cytiva) to remove free PHK67 that was not stained in the exosome membrane. A negative control was prepared by allowing PKH67 fluorescence dye to react with a buffered solution and fractionating the reaction product with a MiniTrap-25 column. The exosomes stained with PKH67 were incubated with pre-cultured mouse macrophages, and then whether the exosomes would be delivered into the cells over time was observed using a fluorescence microscope. Hoechst fluorescence dye (purchased from Thermo Fisher) was used to stain the cell nucleus, and CellMask Orange fluorescence dye (purchased from Thermo Fisher) was used to stain the cytoplasm. As a result of examining whether the exosomes would be delivered into the cells, it was confirmed that the fluorescence-stained exosomes were delivered into the cells and green fluorescence accumulated in the cells over time (FIG. 7).

Example 9: Evaluation of Anti-Inflammatory Effect of *Iris*-Derived Exosomes In order to examine whether the *iris*-derived exosomes prepared in Example 2 exhibit an anti-inflammatory effect, the effect of the *iris*-derived exosomes on the amount of IL-6 production in RAW 264.7 cells, which are mouse macrophages, was evaluated. RAW 264.7 cells suspended in DMEM medium containing 10% FBS were seeded into each well of a 48-well plate to reach a confluency of 80 to 90%. Next, the RAW 264.7 cells were treated with an LPS-containing fresh medium [DMEM containing 1% FBS and 200 nM LPS (lipopolysaccharide)] mixed with the culture media of *iris* callus prepared in Example 1 or the *iris*-derived exosomes prepared in Example 2, and then the RAW 264.7 cells were cultured for 24 hours. Experimental groups for evaluating the anti-inflammatory effect were classified as follows.

(1) Negative control group (indicated as "N.C." in FIG. 8): an experimental group in which RAW 264.7 cells were treated with an LPS-containing medium alone;

(2) Positive control group (indicated as "P.C." in FIG. 8): an experimental group in which RAW 264.7 cells were treated with an LPS-containing medium mixed with dexamethasone (final concentration: 200 M);

(3) Group treated with culture media of *iris* callus (indicated as "*Iris* Callus CM" in FIG. 8): an experimental group in which RAW 264.7 cells were treated with the culture media of *iris* callus (prepared in Example 1) diluted in an LPS-containing medium (treatment concentrations of the culture media of *iris* callus—low concentration: 50 µg/mL, and high concentration: 200 µg/mL); and (4) Group treated with *iris*-derived exosomes: an experimental group in which RAW 264.7 cells were treated with the *iris*-derived exosomes (prepared in Example 2) diluted in an LPS-containing medium (treatment concentrations of the *iris*-derived exosomes—low concentration: 50 µg/mL, and high concentration: 200 µg/mL).

After completion of the culturing the RAW 264.7 cells of each experimental group, the culture supernatant was collected, and the production amount of the inflammatory cytokine IL-6 present in the culture supernatant was measured using an IL-6 ELISA kit. The amount of IL-6 (inflammatory cytokine) produced in the group treated with LPS alone, and the amount of IL-6 produced in each of the experimental groups treated with the LPS-containing media mixed with dexamethasone, the culture media of *iris* callus and the *iris*-derived exosomes, respectively, were measured using an ELISA kit (purchased from R&D Systems) according to the manufacturer's manual (FIG. 8).

Figure 8:
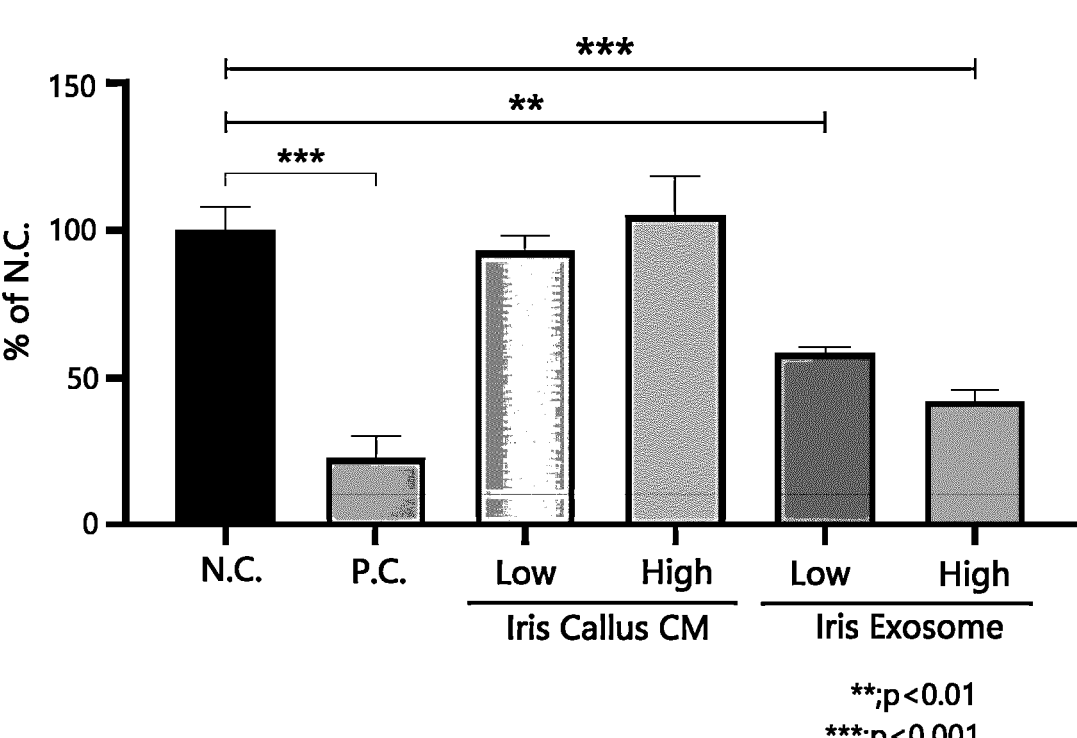
FIG. 8 is a graph showing that IL-6 induced by LPS decreased in a concentration-dependent manner when RAW 264.7 cells were treated with exosomes derived from *iris*.

As shown in FIG. 8, in the experimental group in which the mouse microphage RAW 264.7 cells were treated with LPS plus the *iris*-derived exosomes of the present invention, the production of IL-6 was remarkably inhibited compared to that in the negative control group in which the RAW 264.7 cells were treated with LPS alone, whereas the effect of reducing the production of IL-6 did not appear in the experimental group in which the RAW 264.7 cells were treated with LPS plus the culture media of *iris* callus. In addition, it was confirmed that, as the treatment concentration of the *iris*-derived exosomes of the present invention increased, the production of IL-6 tended to be further inhibited, indicating that the *iris*-derived exosomes of the present invention have a concentration-dependent anti-inflammatory effect.

As can be seen from the above experimental results, the *iris*-derived exosomes of the present invention have an excellent anti-inflammatory effect. Thus, the *iris*-derived exosomes of the present invention are useful as an active ingredient of a pharmaceutical composition for anti-inflammation, wound healing and/or wound healing acceleration.

Although the present invention has been described with reference to the embodiments, the scope of the present invention is not limited to these embodiments. Any person skilled in the art will appreciate that various modifications and changes are possible without departing from the spirit and scope of the present invention and these modifications and changes also fall within the scope of the present invention.

I claim:

1. A method for skin elasticity improvement, skin wrinkle reduction, skin regeneration, skin tone improvement, skin brightness improvement or skin whitening, the method comprising topically administering a composition to a skin of a subject in need thereof, wherein the composition comprises, as an active ingredient, exosomes that are isolated from a conditioned culture medium of *iris* callus.

2. The method of claim 1, wherein the composition is a shampoo, a soap, a rinse, a surfactant-containing cleanser, a cream, a lotion, an ointment, a tonic, a conditioner, a suspension, an emulsion, a paste, a gel, an oil, a wax, a spray, an aerosol, a mist, or a powder.

3. The method of claim 1, wherein the composition is a cream or a lotion.

4. The method of claim 1, wherein the subject is at least one selected from the group consisting of a human, a dog, a cat, a rodent, a horse, a cattle, a monkey and a pig.

5. A method for skin elasticity improvement, skin wrinkle reduction, skin regeneration, skin tone improvement, skin brightness improvement or skin whitening, the method comprising:

(a) (a1) applying a composition comprising, exosomes isolated from a conditioned culture medium of *iris* callus, as an active ingredient to a skin of a subject in need thereof; or (a2) contacting or attaching a patch, a mask pack or a mask sheet, which has the composition applied thereto or soaked therein, to the skin; or (a3) sequentially performing (a1) and (a2).

6. The method of claim 5, wherein the composition is a lotion or a cream in step (a).

7. The method of claim 5, further comprising step (b) removing the patch, the mask pack or the mask sheet from the skin after step (a2) or (a3), and again applying the composition to the skin.

8. The method of claim 7, wherein the composition is a lotion or a cream in step (b).

9. The method of claim 5, wherein the subject is at least one selected from the group consisting of a human, a dog, a cat, a rodent, a horse, a cattle, a monkey and a pig.

10. A method for preventing, suppressing, alleviating, ameliorating or treating inflammation of skin of a subject in need thereof, or healing wound or accelerating wound healing in the subject, the method comprising topically administering a composition to the skin, an inflammatory area or a wounded area of the subject, wherein the composition comprises, as an active ingredient, exosomes isolated from a conditioned culture medium of *iris* callus.

11. The method of claim 10, wherein the composition is topically administered to a target area of the skin, by injection, microneedling, spread, spray, transdermal delivery using a patch or a sheet, iontophoresis, or a combination thereof.

12. The method of claim 10, wherein the composition is an injectable formulation, an infusion formulation, a spray formulation, a liquid formulation, or a patch formulation.

13. The method of claim 10, wherein the subject is at least one selected from the group consisting of a human, a dog, a cat, a rodent, a horse, a cattle, a monkey and a pig.

14. A method for preventing, suppressing, alleviating, ameliorating or treating inflammation of skin of a subject in need thereof, or healing wound or accelerating wound healing in the subject, the method comprising administering an effective amount of a composition to the skin, an inflammatory area or a wounded area of the subject, wherein the composition comprises, as an active ingredient, exosomes isolated from a conditioned culture medium of *iris* callus.

15. The method of claim 14 wherein the composition is administered to the subject by injection, microneedling, or a combination thereof.

16. The method of claim 14, wherein the composition is an injectable formulation, an infusion formulation, or a liquid formulation.

17. The method of claim 14, wherein the subject is at least one selected from the group consisting of a human, a dog, a cat, a rodent, a horse, a cattle, a monkey and a pig.

\* \* \* \* \*